United States Patent [19]

Frenz et al.

[11] Patent Number: 5,783,433
[45] Date of Patent: Jul. 21, 1998

[54] PURIFIED FORMS OF DNASE

[75] Inventors: John Frenz, Millbrae; Mary B. Sliwkowski, San Carlos, both of Calif.

[73] Assignee: Genentech, Inc., South San Francisco, Calif.

[21] Appl. No.: 458,367

[22] Filed: Jun. 2, 1995

Related U.S. Application Data

[63] Continuation of Ser. No. 409,631, Mar. 22, 1995, abandoned, which is a continuation of Ser. No. 348,284, Nov. 30, 1994, abandoned, which is a continuation of Ser. No. 116,186, Sep. 2, 1993, abandoned, which is a continuation of Ser. No. 895,300, Jun. 8, 1992, Pat. No. 5,279,823.

[51] Int. Cl.$^6$ ..................................................... C12N 9/22
[52] U.S. Cl. ........................... 435/199; 435/814; 435/815
[58] Field of Search ................................... 435/199, 814, 435/815

[56] References Cited

U.S. PATENT DOCUMENTS

| | | | |
|---|---|---|---|
| 2,801,956 | 8/1957 | Baumgarten et al. | 195/66 |
| 2,834,710 | 5/1958 | Baumgarten et al. | 167/65 |
| 3,208,908 | 9/1965 | Maxwell et al. | 167/73 |
| 3,663,690 | 5/1972 | Eichel et al. | 424/94 |
| 4,065,355 | 12/1977 | Khouw et al. | 435/199 |
| 5,279,823 | 1/1994 | Frenz et al. | 424/94.61 |

FOREIGN PATENT DOCUMENTS

WO 90/07572  7/1990  WIPO .

OTHER PUBLICATIONS

Ayvazian e al., "The Use of Parenterally Administered Pancreatic Desoxyribonuclease as an Adjunct in the Treatment of Pulmonary Abscesses" *Am. Rev. of Tuberculosis and Pulmonary Diseases* 76(1):1–21 (Jul. 1957).

Bradbury et al., "Peptide amidation" *TIBS* 16:112–115 (1991).

Cacia et al., "Protein sorting by high–performance liquid chromatography" *J. Chromatography* 634:229–239 (1990).

Cliffton et al., "Pancreatic Deoxyribonuclease (Dornase) Aerosol in Treatment of Bronchopulmonary Complications and Tracheitis Sicca" *Cancer* 14(2):414–420 (Mar.–Apr. 1961).

Contreras et al., "Effect of Plastic Containers on Liquid Preservation of Human Granulocytes. I. With and Without Deoxyribonuclease and Hydrocortisone" *Transfusion* 20(5):519–530 (Sep.–Oct. 1980).

Doctor, V.M., "Studies on the Purification and Properties of Human Plasma Deoxyribonuclease I" *Archives of Biochem. and Biophysics* 103:286–290 (1963).

Eipper et al., "Peptide α–Amidation" *Ann. Rev. Physiol.* 50:333–344 (1988).

Farber et al., "Enzymatic Debridement" *J. of Thoracic Surgery* pp. 45–54 (1953).

Frenz et al., "Characterization of Human Growth Hormone by Capillary Electrophoresis" *J. Chromatography* 480:379–391 (1990).

Funakoshi et al., "Clinical Studies on Human Pancreatic Deoxyribonuclease I" *Japanese Society of Gastroenterology* 14(1):48–54 (Feb. 1979).

Funakoshi et al., "Purification and Properties of Human Pancreatic Deoxyribonuclease 1" *J. Biochem.* 82(6):1771–1777 (1977).

Hubbard et al., "A preliminary study of aerosolized recombinant human deoxyribonuclease I in the treatment of cystic fibrosis" *New England J. of Medicine* 326 (12) : 812–815 (Mar. 19, 1992).

(List continued on next page.)

*Primary Examiner*—Rebecca E. Prouty
*Attorney, Agent, or Firm*—Sean A. Johnston

[57] ABSTRACT

The present invention provides the identification and characterization of two components of a recombinant preparation of DNase. These components are the purified deamidated and non-deamidated human DNases. Taught herein are the separation of these components and the use of the non-deamidated species as a pharmaceutical per se, and in particular in compositions wherein the species is disclosed within a plastic vial, for use in administering to patients suffering from pulmonary distress.

3 Claims, 10 Drawing Sheets

OTHER PUBLICATIONS

Ito et al., "Human Urine DNase I: Immunological Identity with Human Pancreatic DNase I, and Enzymic and Protochemical Properties of the Enzyme" *J. Biochem.* 95(5):1399–1406 (1984).

Johnson et al., "The Intravenous Injection of Bovine Crystalline Pancreatic Desoxyribonuclease into Patients" *J. Clin. Invest.* 33:1670–1686 (1954).

Kossiakoff, A.A., "Tertiary Structure Is a Principal Determinant to Protein Deamidation" *Science* 240:191–194 (1988).

Liao et al., "Bovine Pancreatic Deoxyribonuclease A" *Journal of Biological Chemistry* 248(4):1489–1495 (1973).

Liao, Ta–Hsiu, "Bovine Pancreatic Deoxyribonuclease D" *Journal of Biological Chemistry* 249:2354–2356 (1974).

Liao, Ta–Hsiu, "Multiple forms of deoxyribonuclease I" *Mol. and Cell. Biochem.* 34:15–22 (1981).

Lourenco et al., "Clinical Aerosols. II. Therapeutic Aerosols" *Arch. Intern. Med.* 142:2299–2308 (1982).

Love et al., "The Relationship between Human Serum and Human Pancreatic DNase I" *J. of Biol. Chem.* 254(24):12588–12594 (Dec. 25, 1979).

Markey, Francis, "Rapid purification of dexyribonuclease I using fast protein liquid chromatography" *FEBS Letters* 167(1):155–159 (1984).

Murai et al., "Purification and Properties of Deoxyribonuclease from Human Urine" *Biochimica et Biophysica Acta* 517:186–194 (1978).

Nefsky et al., "Preparation of immobilized monmeric actin and its use in the isolation of protease–free and ribonuclease–free pancreatic deoxyribonuclease" *European Journal of Biochemistry* 179:215–219 (1989).

Paudel et al., "Comparison of the Three Primary Structures of Deoxyribonuclease Isolated from Bovine, Ovine, and Porcine Pancreas" *J. of Biol. Chem.* 261(34):16012–16017 (Dec. 5, 1986).

Paudel et al., "Purification, Characterization, and the Complete Amino Acid Sequence of Porcine Pancreatic Deoxyribonuclease" *J. of Biol. Chem.* 261(34):16006–16011 (Dec. 5, 1986).

Potter et al., "The Composition of Pulmonary Secretions from Patients With and Without Cystic Fibrosis" *Am. J. Dis. Child.* 100:493–495 (1960).

Raskin, Philip, "Bronchospasm After Inhalation of Pancreatic Dornase" *Am. Rev. of Respiratory Disease* 98:697–698 (1968).

Rosenstreich et al., "A Human Urine–Derived Interleukin 1 Inhibitor" *Journal of Experimental Medicine* 168:1767–1779 (Nov. 1988).

Salnikow et al., "Bovine Pancreatic Deoxyribonucleases A and C" *J. of Biol. Chem.* 248(5):1499–1501 (Mar. 10, 1973).

Salomon et al., "Aerosols of Pancreatic Dornase in Brochopulmonary Disease" *Annals of Allergy* pp. 71–79 (Jan.–Feb. 1954).

Segal et al., "Pancreatic Dornase Aerosols in Brochopulmonary Disease" *Annals N.Y. Acad. Sci.* 68:138–143 (1957).

Shak et al., "Recombinant Human DNase I Reduces the Viscosity of Cystic Fibrosis Sputum" *Proc. Natl. Acad. Sci. USA* 87:9188–9192 (Dec. 1990).

Shields et al., "Cloning of part of the gene for bovine deoxyribonuclease I" *Biochemical Society Transactions* 16:195–196 (1988).

Teshima et al., "Deamidatio of Soluble CDr at Asparagine–52 Results in reduced Binding Capacity for the HIV–1 Envelope Glycoprotein gp120" *Biochemistry* 30:3916–3922 (1991).

Wang et al., "Preparation of Protease–free and Ribonuclease–free Pancreatic Deoxyribonuclease" *J. of Biol. Chem.* 253(20):7216–7219 (Oct. 25, 1978).

Wright, H. Tonie, "Sequence and structure determinants of the nonenzymatic deamidation of asparagine and glutamine residues in proteins" *Protein Engineering* 4(3):283–294 (1991).

Wroblewski et al., "Presence of Desoxyribonuclease Activity in Human Serum" *P.S.E.B.M.* 74:443–445 (1950).

Yeager, Jr., Henry, "Tracheobronchial Secretions" *Am. J. of Medicine* 50:493–509 (Apr. 1971).

Borchert et al., "Accelerated Extractable Studies of Borosilicate Glass Containers" *Journal of Parenteral Science & Technology* 43(2):67–79 (Mar.–Apr. 1989).

```
  1 TCCTGCACAG GCAGTGCCTT GAAGTGCTTC TTCAGAGACC TTTCTTCATA
    AGGACGTGTC CGTCACGGAA CTTCACGAAG AAGTCTCTGG AAAGAAGTAT
  1 SerCysThrG lySerAlaLe uLysCysPhe PheArgAspL euSerSerAM

101 ATATTCCAGA TTCTTGACAG CATTCTCGTC ATCTCTGAGG ACATCACCAT
    TATAAGGTCT AAGAACTGTC GTAAGAGCAG TAGAGACTCC TGTAGTGGTA
 35    IleProAs pSerOP*Gln HisSerArgH isLeuOP*Gl yHisHisHis

201 GGCCCTACTG CAGGGGGCCG TGTCCCTGAA GATCGCAGCC TTCAACATCC
    CCGGGATGAC GTCCCCCGGC ACAGGGACTT CTAGCGTCGG AAGTTGTAGG
 68 AlaLeuLeu  GlnGlyAlaV alSerLeuLy sIleAlaAla PheAsnIleG

301 GTGCAGATCC TGAGCCGCTA TGACATCGCC CTGGTCCAGG AGGTCAGAGA
    CACGTCTAGG ACTCGGCGAT ACTGTAGCGG GACCAGGTCC TCCAGTCTCT
101 ValGlnIleL euSerArgTy rAspIleAla LeuValGlnG luValArgAs

401 CACCAGACAC CTATCACTAC GTGGTCAGTG AGCCACTGGG ACGGAACAGC
    GTGGTCTGTG GATAGTGATG CACCAGTCAC TCGGTGACCC TGCCTTGTCG
135    ProAspTh rTyrHisTyr ValValSerG luProLeuGl yArgAsnSer

501 GGACAGCTAC TACTACGATG ATGGCTGCGA GCCCTGCGGG AACGACACCT
    CCTGTCGATG ATGATGCTAC TACCGACGCT CGGGACGCCC TTGCTGTGGA
168    AspSerTyr TyrTyrAspA spGlyCysGl uProCysGly AsnAspThrP

601 AGGGAGTTTG CCATTGTTCC CCTGCATGCG GCCCCGGGGG ACGCAGTAGC
    TCCCTCAAAC GGTAACAAGG GGACGTACGC CGGGGCCCCC TGCGTCATCG
201 ArgGluPheA laIleValPr oLeuHisAla AlaProGlyA spAlaValAl

701 GCTTGGAGGA CGTCATGTTG ATGGGCGACT TCAATGCGGG CTGCAGCTAT
    CGAACCTCCT GCAGTACAAC TACCCGCTGA AGTTACGCCC GACGTCGATA
235    LeuGluAs pValMetLeu MetGlyAspP heAsnAlaGl yCysSerTyr

801 CCAGTGGCTG ATCCCCGACA GCGCTGACAC CACAGCTACA CCCACGCACT
    GGTCACCGAC TAGGGGCTGT CGCGACTGTG GTGTCGATGT GGGTGCGTGA
268. GlnTrpLeu  IleProAspS erAlaAspTh rThrAlaThr ProThrHisC

901 GTTCCCGACT CGGCTCTTCC CTTTAACTTC CAGGCTGCCT ATGGCCTGAG
    CAAGGGCTGA GCCGAGAAGG GAAATTGAAG GTCCGACGGA TACCGGACTC
301 ValProAspS erAlaLeuPr oPheAsnPhe GlnAlaAlaT yrGlyLeuSe

1001 TGAACTGAGC AGCCCCTCCC CACACCAGTT GAACTGCAG
     ACTTGACTCG TCGGGGAGGG GTGTGGTCAA CTTGACGTC
 335    LysOP*Al aAlaProPro HisThrSerO P*ThrAla
```

FIG. IA

```
GACTACTTTT  TTTTCTTTAA  GCAGCAAAAG  GAGAAAATTG  TCATCAAAGG
CTGATGAAAA  AAAAGAAATT  CGTCGTTTTC  CTCTTTTAAC  AGTAGTTTCC
*ThrThrPhe  PheSerLeuS  erSerLysAr  gArgLysLeu  SerSerLysAsp

CATCTCAGGA  TGAGGGGCAT  GAAGCTGCTG  GGGGCGCTGC  TGGCACTGGC
GTAGAGTCCT  ACTCCCCGTA  CTTCGACGAC  CCCCGCGACG  ACCGTGACCG
HisLeuArgM  etArgGlyMe  tLysLeuLeu  GlyAlaLeuL  euAlaLeuAla

AGACATTTGG  GGAGACCAAG  ATGTCCAATG  CCACCCTCGT  CAGCTACATT
TCTGTAAACC  CCTCTGGTTC  TACAGGTTAC  GGTGGGAGCA  GTCGATGTAA
lnThrPheGl  yGluThrLys  MetSerAsnA  laThrLeuVa  lSerTyrIle

CAGCCACCTG  ACTGCCGTGG  GGAAGCTGCT  GGACAACCTC  AATCAGGATG
GTCGGTGGAC  TGACGGCACC  CCTTCGACGA  CCTGTTGGAG  TTAGTCCTAC
pSerHisLeu  ThrAlaValG  lyLysLeuLe  uAspAsnLeu  AsnGlnAspAla

TATAAGGAGC  GCTACCTGTT  CGTGTACAGG  CCTGACCAGG  TGTCTGCGGT
ATATTCCTCG  CGATGGACAA  GCACATGTCC  GGACTGGTCC  ACAGACGCCA
TyrLysGluA  rgTyrLeuPh  eValTyrArg  ProAspGlnV  alSerAlaVal

TCAACCGAGA  GCCAGCCATT  GTCAGGTTCT  TCTCCCGGTT  CACAGAGGTC
AGTTGGCTCT  CGGTCGGTAA  CAGTCCAAGA  AGAGGGCCAA  GTGTCTCCAG
heAsnArgGl  uProAlaIle  ValArgPheP  heSerArgPh  eThrGluVal

CGAGATCGAC  GCTCTCTATG  ACGTCTACCT  GGATGTCCAA  GAGAAATGGG
GCTCTAGCTG  CGAGAGATAC  TGCAGATGGA  CCTACAGGTT  CTCTTTACCC
aGluIleAsp  AlaLeuTyrA  spValTyrLe  uAspValGln  GluLysTrpGly

GTGAGACCCT  CCCAGTGGTC  ATCCATCCGC  CTGTGGACAA  GCCCCACCTT
CACTCTGGGA  GGGTCACCAG  TAGGTAGGCG  GACACCTGTT  CGGGGTGGAA
ValArgProS  erGlnTrpSe  rSerIleArg  LeuTrpThrS  erProThrPhe

GTGCCTATGA  CAGGATCGTG  GTTGCAGGGA  TGCTGCTCCG  AGGCGCCGTT
CACGGATACT  GTCCTAGCAC  CAACGTCCCT  ACGACGAGGC  TCCGCGGCAA
ysAlaTyrAs  pArgIleVal  ValAlaGlyM  etLeuLeuAr  gGlyAlaVal

TGACCAACTG  GCCCAAGCCA  TCAGTGACCA  CTATCCAGTG  GAGGTGATGC
ACTGGTTGAC  CGGGTTCGGT  AGTCACTGGT  GATAGGTCAC  CTCCACTACG
rAspGlnLeu  AlaGlnAlaI  leSerAspHi  sTyrProVal  GluValMetLeu
```

FIG. 1B

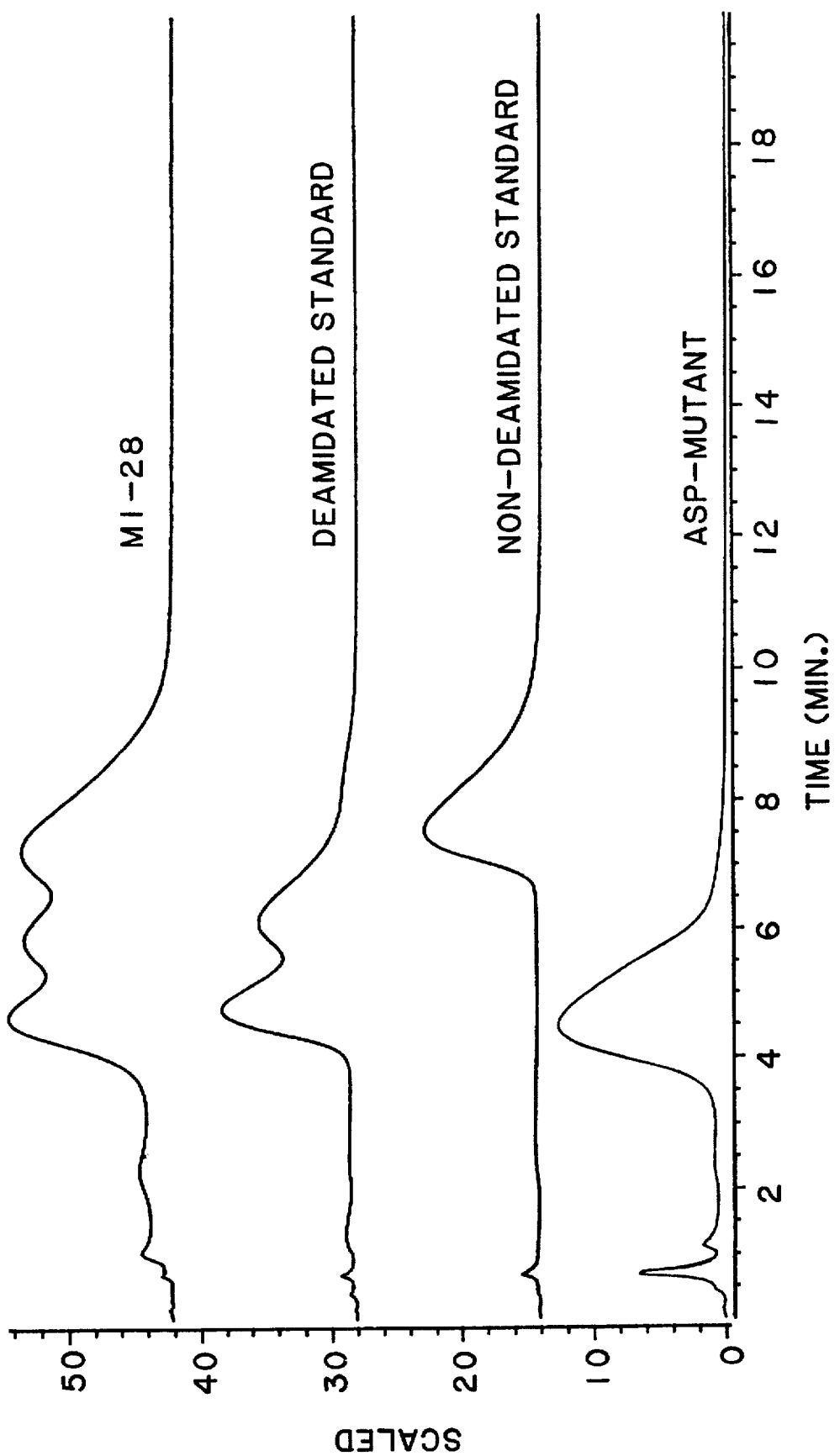

PURIFIED FORMS OF DNASE

This is a continuation of applications Ser. No. 08/409,631, filed on Mar. 22, 1995, now abandoned, which is a continuation of Ser. No. 08/348,284, filed on Nov. 30, 1994, now abandoned, which is a continuation of Ser. No. 08/116,186, filed on Sep. 2, 1993, now abandoned, which is a continuation of Ser. No. 07/895,300, filed on Jun. 8, 1992, issued as U.S. Pat. No. 5,279,823, which applications are incorporated herein by reference and to which application(s) priority is claimed under 35 USC § 120.

RELATED PATENT APPLICATIONS

The present application is related in subject matter to the disclosure contained in U.S. patent application Ser. No. 07/448,038, filed 8 Dec. 1989 and U.S. patent application Ser. No. 07/289,958, filed 23 Dec. 1988. The subject matter of those applications is in the public domain by virtue of the publication, inter alia, of the PCT counterpart on or about 12 Jul. 1990 as International Patent Application Publication No. WO 90/07572. The content of these prior applications is hereby expressly incorporated by reference herein.

FIELD OF THE INVENTION

The present invention is related to results obtained from research on deoxyribonuclease (DNase), a phosphodiesterase that is capable of hydrolyzing polydeoxyribonucleic acid. It relates generally to the separation of several forms of said DNase, to these forms per se, to pharmaceutical compositions by which their utility can be exploited clinically, and to methods of using these DNases and compositions thereof.

BACKGROUND OF THE INVENTION

DNase is a phosphodiesterase capable of hydrolyzing polydeoxyribonucleic acid. DNase has been purified from various species to various degrees. The complete amino acid sequence for a mammalian DNase was first made available in 1973. See e.g., Liao, et al., J. Biol. Chem. 248:1489 (1973).

DNase has a number of known utilities and has been used for therapeutic purposes. Its principal therapeutic use has been to reduce the viscoelasticity of pulmonary secretions in such diseases as pneumonia and cystic fibrosis, thereby aiding in the clearing of respiratory airways. See e.g., Lourenco, et al., Arch. Intern. Med. 142:2299 (1982); Shak, et al., Proc. Nat. Acad. Sci. 87:9188 (1990); Hubbard, et al., New Engl. J. Med. 325:812 (1992).

DNA encoding human DNase I has been isolated and sequenced and that DNA has been expressed in recombinant host cells, thereby enabling the production of human DNase in commercially useful quantities. See e.g., Shak, et al., Proc. Nat. Acad. Sci. 87:9188–9192 (1990). Recombinant human DNase (rhDNase) has been found to be useful clinically, especially in purified form such that the DNase is free from proteases and other proteins with which it is ordinarily associated in nature. See e.g., Hubbard, et al., New Engl. J. Med. 326:812 (1992).

The means and methods by which human DNase can be obtained in pharmaceutically effective form is described in the patent applications cited above. Various specific methods for the purification of DNase are known in the art. See e.g., Khouw, et al., U.S. Pat. No. 4,065,355 (issued 27 Dec. 1977); Markey, FEBS Letters 167:155 (1984); Nefsky, et al., Eur. J. Biochem. 179:215 (1989).

Although it was not appreciated at the time the above-referenced patent applications were filed, the DNase product obtained from cultures of recombinant host cells typically comprises a mixture of deamidated and non-deamidated forms of DNase. The existence of deamidated forms of DNase remained unappreciated notwithstanding that the phenomenon of deamidation of asparagine and glutamine residues in some proteins is known. See e.g., Eipper et al., Ann. Rev. Physiol. 50:333 (1988); Kossiakoff, Science 240:191 (1988); Bradbury et al., Trends in Biochem. Sci. 16:112 (1991); and Wright, Protein Engineering 4:283 (1991);

The present invention is predicated upon the previously unappreciated fact that recombinant human DNase may exist as a mixture of deamidated and non-deamidated forms. Using the methods of the present invention, it has been found that deamidated human DNase is less active enzymatically than non-deamidated human DNase. Thus, the presence of the deamidated DNase and non-deamidated DNase together in a mixture, and the potential for further deamidation occurring, such as has been found to occur upon in vitro storage of preparations of human DNase, may complicate efforts to provide consistent uniformity in a DNase product being administered clinically. Therefore, as the existence and characteristics of deamidated DNase were not known prior to the present invention, the methods for identifying deamidated DNase and separating it from preparations of DNase in which it may be found were unobvious at the time this invention was made.

SUMMARY OF THE INVENTION

The present invention is directed to processes for separating the deamidated and non-deamidated human DNase forms from a mixture thereof. This process in preferred embodiments comprises subjecting the mixture to chromatography using a resin, or other support medium, having bound thereto a cationic polymer such as heparin or a non-hydrolyzable deoxyribonucleic acid (DNA) analog, or chromatography using a so-called tentacle cation exchange resin. The present invention also is directed to the use of those chromatographic methods with non-human DNases, such as bovine DNase.

The present invention also is directed to deamidated human DNase as a purified product, substantially free of non-deamidated human DNase.

The present invention also is directed to non-deamidated human DNase as a purified product, substantially free of deamidated human DNase. It has been found herein that purified non-deamidated human DNase is fully enzymatically active as compared with deamidated human DNase.

The present invention also is directed to pharmaceutical compositions consisting of either purified deamidated human DNase or purified non-deamidated human DNase as the active principle, optionally together with a pharmaceutically acceptable excipient.

The present invention also is directed to a method comprising administering a therapeutically effective amount of purified deamidated human DNase or purified non-deamidated human DNase for the treatment of a patient, for example those having an accumulation of viscous, DNA-containing material. The administration of such purified DNases preferably is effected by direct inhalation into the lungs.

The present invention is particularly directed to a method of treating a patient having a pulmonary disease such as chronic bronchitis, cystic fibrosis, or emphysema, that comprises administering a therapeutically effective amount of purified non-deamidated human DNase, preferably directly into the airway passages.

The present invention also is directed to pharmaceutical compositions comprising non-deamidated human DNase that are disposed within a plastic vial, optionally in the presence of a pharmaceutically acceptable excipient.

BRIEF DESCRIPTION OF THE DRAWINGS

FIG. 1 depicts the amino acid (SEQ. ID. NO. 1) and DNA sequences (SEQ. ID. NO. 2) of human DNase I. The native signal sequence is underlined, the potential initiation codons are circled, and the mature sequence is bracketed.

FIG. 9 shows chromatograms of several human DNase samples fractionated on an immobilized DNA analog column. The sample designated "M1-28" is a preparation of human DNase obtained from a culture of Chinese hamster ovary (CHO) cells transformed with DNA encoding native human DNase I. The sample designated "Deamidated Standard" is purified deamidated human DNase. The sample designated "Non-deamidated standard" refers to purified non-deamidated human DNase. Purified deamidated human DNase and purified non-deamidated human DNase was prepared by TCX chromatography. The sample designated "DNase ASP Mutant" is DNase having an aspartic acid residue (rather than an asparagine residue) at amino acid position 74.

DETAILED DESCRIPTION

A. Definitions

Figure 2:
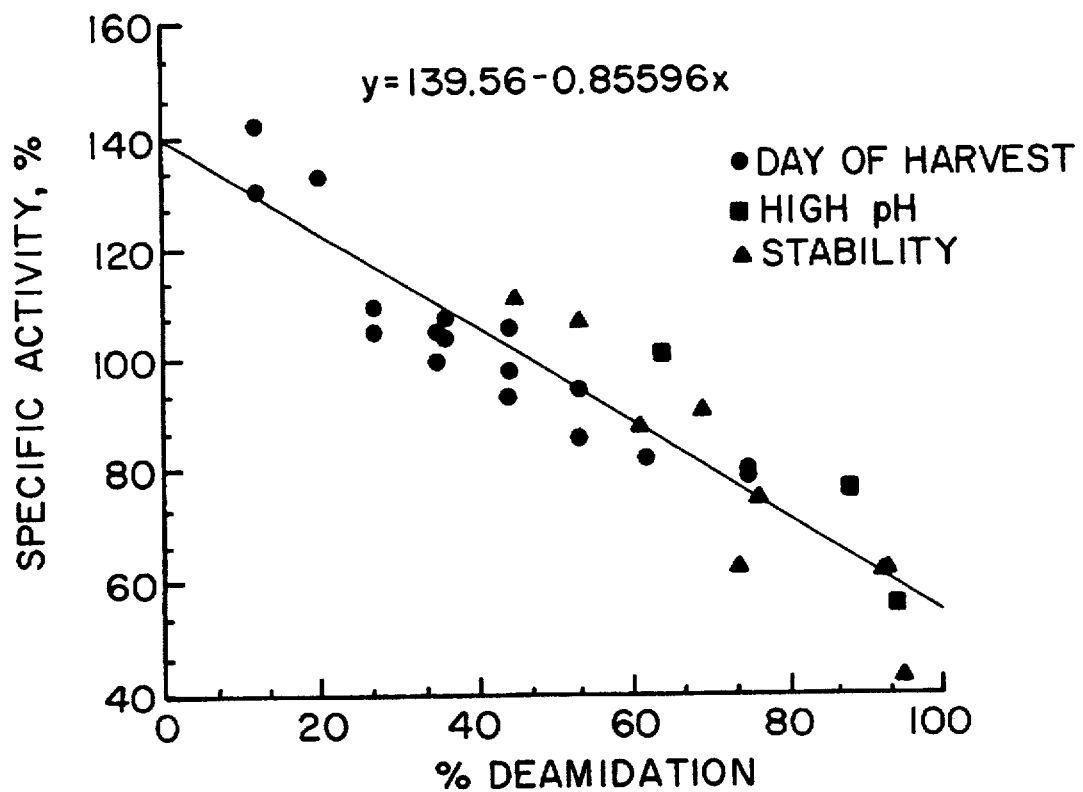
FIG. 2 depicts the correlation between enzymatic activity and extent of deamidation of samples of human DNase. Specific activity was determined by normalizing the DNase activity as determined by a methyl green (MG) assay (in concentration units relative to a standard curve) to the DNase concentration measured by an enzyme-linked immunoabsorbent assay (ELISA). Percent deamidation was determined by tryptic mapping. "Day of Harvest" samples of human DNase were purified from a culture of recombinant Chinese hamster ovary (CHO) cells expressing DNA encoding human DNase I. Such samples were taken at 3, 5, 7, 9, 11, 13, and 20 days after the culture was started. "High pH" samples were day 13 samples of purified DNase that were incubated in vitro for two days at pH 8 at 370. "Stability" samples were day 13 samples of purified DNase that were stored in vitro at 5°, 25°, or 37° C. for various periods of time.

By the term "human DNase" herein is meant a polypeptide having the amino acid sequence of human mature DNase I set forth in FIG. 1 as well as amino acid sequence variants thereof (including allelic variants) that are enzymatically active in hydrolyzing DNA. Thus, the term "human DNase" herein denotes a broad definition of those materials disclosed and prepared in the patent applications described above.

The term "human DNase" necessarily embraces native mature human DNase having an asparagine (Asn) residue at amino acid position 74 of the polypeptide. That asparagine has been found herein to be susceptible to deamidation, which deamidation may produce a mixture of deamidated and non-deamidated forms of human DNase. Instead of the Asn residue at amino acid position 74, deamidated DNase has an aspartic acid (Asp) or an iso-aspartate (iso-Asp) residue (see FIG. 4).

The term "deamidated human DNase" as used herein thus means human DNase that is deamidated at the asparagine residue that occurs at position 74 in the amino acid sequence of native mature human DNase. It has been found that deamidated human DNase may arise during the production of human DNase by recombinant means, and may be found in preparations of human DNase obtained from recombinant host cells. Additionally, deamidated human DNase may arise upon in vitro storage of non-deamidated human DNase.

Although the asparagine residue at amino acid position 7 in the amino acid sequence of native mature human DNase also may be deamidated (in addition to the asparagine residue at amino acid position 74), such doubly deamidated DNase has been found to be enzymatically inactive.

The term "mixture" as used herein in reference to preparations of human DNase means the presence of both deamidated and non-deamidated forms of human DNase. It has been found, for example, that in preparations of human DNase obtained from recombinant expression, as much as about 50% to 80% or more of the human DNase is deamidated.

The term "purified deamidated human DNase" as used herein means deamidated human DNase that is substantially free of non-deamidated human DNase. In other words, non-deamidated human DNase will comprise less than about 10%, preferably less than about 5%, and most preferably less than about 1% by weight of the total DNase in the purified deamidated human DNase composition.

The term "purified non-deamidated human DNase" as used herein means non-deamidated human DNase that is substantially free of deamidated human DNase. In other words, deamidated human DNase will comprise less than about 25%, preferably less than about 5%, and most preferably less than about 1% by weight of the total DNase in the purified non-deamidated human DNase composition.

By the term "excipient" herein is meant a pharmaceutically acceptable material that is employed together with DNase for the proper and successful administration of the DNase to a patient. Suitable excipients are well known in the art, and are described, for example, in the *Physicians Desk Reference*, the *Merck Index*, and *Remington's Pharmaceutical Sciences*.

A preferred formulation for human DNase is a buffered or unbuffered aqueous solution, and preferably is an isotonic salt solution such as 150 mM sodium chloride containing 1.0 mM calcium chloride at pH 7. These solutions are particularly adaptable for use in commercially-available nebulizers including jet nebulizers and ultrasonic nebulizers useful for administration, for example directly into the airways or lungs of an affected patient. Reference is made to the above-identified patent applications for further detail concerning how human DNase can be formulated and administered for effective use.

By the term "therapeutically effective amount" herein, is meant dosages of from about 1 µg to about 100 mg of human DNase per kilogram of body weight of the patient, administered within pharmaceutical compositions, as described herein. The therapeutically effective amount of human DNase will depend, for example, upon the therapeutic objectives, the route of administration, and the condition of the patient. Accordingly, it will be necessary for the therapist to titer the dosage and modify the route of administration as required to obtain the optimal therapeutic effect. In view of the differences in enzymatic activity between deamidated and non-deamidated DNases described herein, it may be that the amount of purified non-deamidated DNase required to achieve a therapeutic effect will be less than the amount of purified deamidated human DNase or a mixture of the two forms necessary to achieve the same effect under the same conditions.

The purified DNases hereof, particularly the non-deamidated form, are employed for enzymatic alteration of the viscoelasticity of mucous. Such purified human DNases are particularly useful for the treatment of patients with pulmonary disease who have abnormal viscous, purulent secretions and conditions such as acute or chronic bronchial pulmonary disease, including infectious pneumonia, bronchitis or tracheobronchitis, bronchiectasis, cystic fibrosis, asthma, tuberculosis, and fungal infections. For such therapies, a solution or finely divided dry preparation of purified deamidated human DNase or purified non-deamidated human DNase is instilled in conventional fashion into the bronchi, for example by aerosolization.

B. Preferred Embodiments

After the successful cloning and expression of human DNase in recombinant host cells, it was discovered after substantial research that the DNase product obtained from such recombinant expression typically existed as a mixture of as then yet undefined components. In particular, isoelectric focusing (IEF) analysis of human DNase purified from cultures of recombinant Chinese hamster ovary (CHO) cells revealed a complex pattern of DNase species. The various DNase species were determined to result from several post-translational modifications of the DNase, including deamidation.

Two assays were used to determine the presence and extent of deamidated DNase in such preparations. One method involved tryptic digestion of the starting preparation of DNase and analysis of the resulting peptides by reverse phase HPLC. In this method, the amount of deamidated DNase in the starting preparation was determined by measuring the quantities of six deamidation-indicating tryptic peptides.

The other method involved chromatography of the starting preparation of DNase on a tentacle cation exchange (TCX) column. It was discovered that the TCX column is capable of resolving deamidated human DNase and non-deamidated human DNase, such that each form of DNase could be effectively separated from the other, and obtained in purified form. In this method, the amount of deamidated and non-deamidated DNase in the starting preparation was determined by measuring on chromatograms the peak areas corresponding to the separated forms of DNase.

Although these two methods are about equally effective in determining and quantitating deamidated DNase, the TCX method is especially efficient, requiring far less time and labor than the other method. Moreover, TCX chromatography provides a means for separating deamidated and non-deamidated forms of DNase, whereas conventional cation exchange resins and various other chromatography resins that were analyzed were not capable of such separation.

The general principles of TCX chromatography have been described, for example, by Miller, J. Chromatography 510:133 (1990); Janzen et al., J. Chromatography 522:77 (1990); and Hearn et al., J. Chromatography 548:117 (1991). Without limiting the invention to any particular mechanism or theory of operation, it is believed that the Asn-74 residue in human DNase that is susceptible to deamidation is located within the DNA-binding groove of the enzyme, by analogy to the known crystal structure of bovine DNase. The DNA-binding groove contains basic amino acid residues (in order to bind DNA) and this groove apparently is accessible to the ligands of the tentacle cation exchange resin but not to the much shorter ligands of conventional cation exchange resins. Presumably the ligands of the tentacle cation exchange resin mimic natural nucleic acid substrates. Therefore, it is expected that tentacle action exchange chromatography will be useful for the purification of other nucleases, such as ribonuclease (RNase) or restriction endonucleases, as well as DNA binding proteins.

Alternatively, the separation of deamidated and non-deamidated forms of DNase may be accomplished by chromatography using a resin or other support matrix containing covalently bound cationic polymers such as heparin or a synthetic non-hydrolyzable DNA analog. Immobilized heparin chromatography columns are commercially available (for example, from Toso Haas Co., Montgomeryville, Pa.). Non-hydrolyzable DNA analogs have been described, for example, by Spitzer et al., Nuc. Acid. Res. 16:11691 (1988). An immobilized non-hydrolyzable DNA analog column is conveniently prepared by synthesizing such a DNA analog with an amino acid group at the 3'-end of one or both of its complementary strands. The amino group is then available for coupling to an epoxy-activated column, as described, for example, in literature published by Rainin Biochemical LC Products (Woburn, Mass.).

Following the successful separation of deamidated and non-deamidated human DNases according to the methods of the present invention, it was found that deamidated human DNase has diminished enzymatic activity as compared to non-deamidated human DNase, as determined by a methyl green (MG) assay. Kurnick, Arch. Biochem. 29:41 (1950). It was found that deamidated human DNase exhibits just over half of the enzymatic activity of non-deamidated human DNase. Thus, by combining the purified deamidated DNases and the purified non-deamidated DNase of the present invention in various proportions, it is possible to prepare pharmaceutical compositions of human DNase having any desired specific activity in the range between the specific activities of the individual components, as may be optimal for treating particular disorders.

The following examples are offered by way of illustration only and are not intended to limit the invention in any manner. All patent and literature references cited throughout the specification are expressly incorporated herein.

C. Examples

1. Tryptic Mapping.

The procedure used for tryptic mapping of human DNase is summarized as follows:

Step 1. Bring concentration of 1 mg sample of DNase to 4 mg/ml by concentration on Amicon Centricon-10 device or by dilution with excipient. Final volume: 250 µl.

Step 2. Add 250 µl of pretreatment buffer (40 mM BisTris, 10 mM EGTA, pH 6.0) to sample. Incubate 1 hour at 37°.

Step 3. Buffer exchange sample into digest buffer (100 mM Tris, pH 8) using Pharmacia NAP-5 column. Final volume: 1 ml.

Step 4. Add 10 µl trypsin solution (1 mg/ml trypsin, 1 mM HCl) to sample and incubate 2 hours at 37°.

Step 5. Add second 10 µl aliquot of trypsin solution to sample and incubate additional 2 hours at 37°.

Step 6. Stop digestion by addition of 6 µl trifluoroacetic acid (TFA). Store samples at or below 5° until chromatographed.

Step 7. Separate the peptide mixture by HPLC under the following conditions:

Column: Nucleosil C18, 5 µm, 100 Å, 2.0×150 mm (Alltech, Co., Deerfield, Ill.). Column temperature: 40°. Eluent A: 0.12% TFA in water. Eluent B: 0.10% TFA in acetonitrile. Gradient profile:

| Time (min) | % A | % B |
|---|---|---|
| 0 | 100 | 0 |
| 5 | 100 | 0 |
| 65 | 40 | 60 |
| 69 | 5 | 95 |
| 70 | 5 | 95 |

Flow rate: 0.25 ml/min. Sample injection volume: 250 µl. Post-run column reequilibration time at 100% A: 20 min. Autosampler compartment temperature: 5°. Detection: Absorbance at 214 and 280 nm.

Step 8. Identify T7, (D)T7, T7-8, (D)T7-8, T6-7-8, and T6-7 tryptic peptides by retention time comparison with standard.

Step 9. Integrate chromatogram obtained at 280 nm. Check quality of integration by inspection of baseline and separation of closely eluting peaks. Special attention must be paid to the early-eluting T7 and (D)T7 peptides that may not be well-resolved.

Step 10. Normalize peak areas of the six reporter peptides to tyrosine content. Peptides T7, (D)T7, T7-8, and (D)T7-8 each contain a single Tyr residue, while T6-7-8 and T6-7 contain three Tyr residues. Calculate the proportion of deamidated species based on the normalized peak areas of (D)T7, (D)T7-8, T6-7-8, and T6-7 relative to the total normalized peak areas of the six peptides.

One milligram of DNase in a volume of 250 µl is required in order to accurately carry out the tryptic mapping method for determination of deamidated DNase according to the procedure outlined above. Hence, the initial sample preparation for this method requires either concentration or dilution of the sample to achieve that result. DNase in the presence of calcium is highly resistant to proteases, including trypsin. Therefore the next step in the procedure is to partially remove calcium ions by treatment with [ethylene bis(oxyethylenenitrilo)] tetraacetic acid (EGTA). Overtreatment with EGTA can denature and aggregate DNase, so this step must be performed with care. The EGTA-treated sample in a volume of 0.5 ml is then exchanged into 1 ml of the digest buffer, trypsin added, and the sample incubated at 37° for two hours. A second aliquot of trypsin is then added and the sample incubated an additional two hours. Digestion is stopped by acidification, and the sample is either stored for later analysis or loaded on the HPLC column directly.

Figure 3:
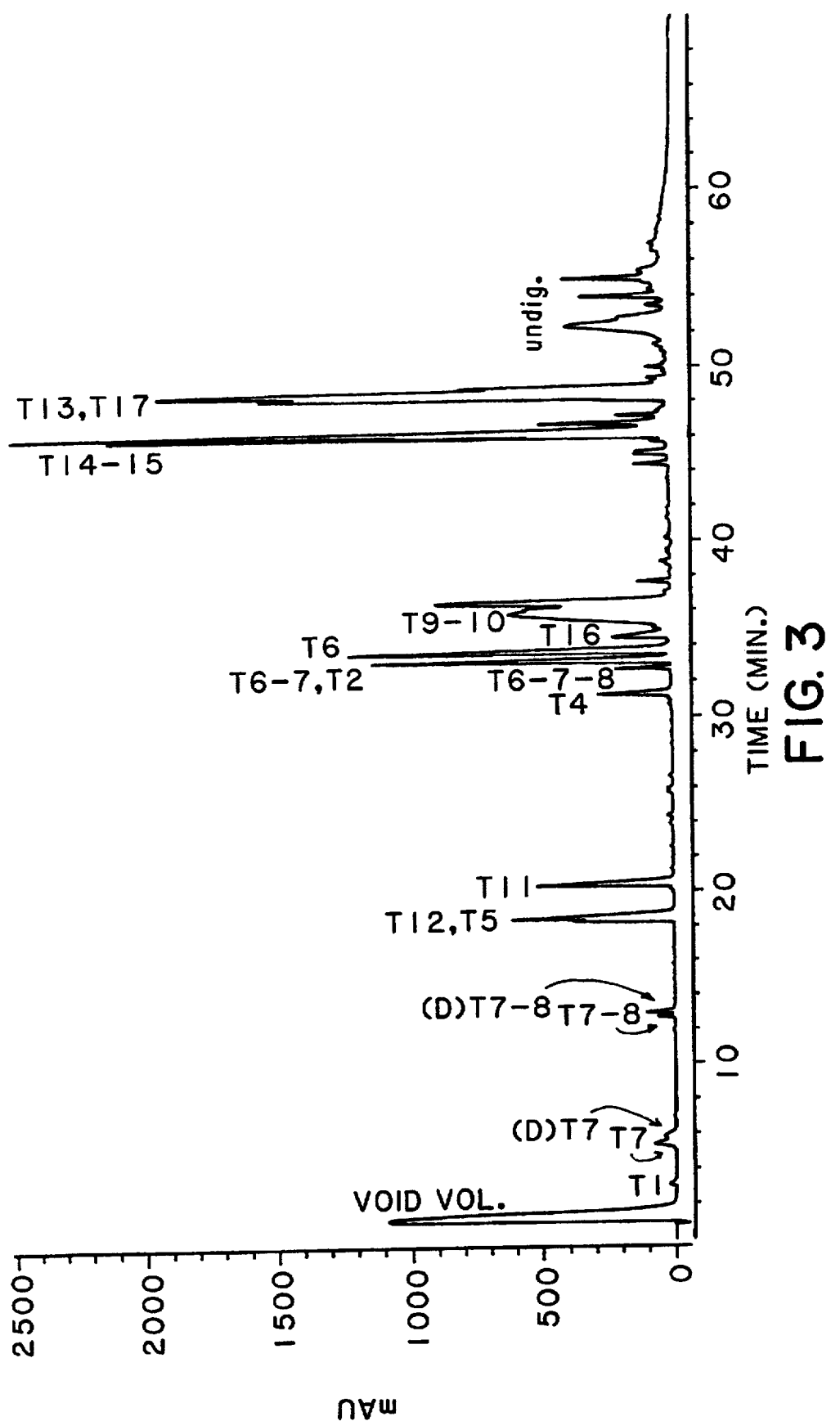
FIG. 3 is an example of a tryptic map of DNase employed for determination of the extent of deamidation. The sample shown here is 65% deamidated DNase. "mAU" indicates milli-absorbance units at 214 nM.

250 µl (250 µg) of the peptide mixture resulting from the tryptic digestion is separated on a reversed phase HPLC column according to the conditions outlined above. A typical tryptic map of human DNase is shown in FIG. 3. HPLC was performed with a Hewlett-Packard model 1090M HPLC. The column effluent was monitored simultaneously at 214 and 280 nm by the diode array detector that is a feature of this instrument. Since the early portion of the peptide map is critical to the quantitation of deamidated DNase, as described below, other instruments with larger gradient delay and other extra-column volumes may not be suited to this analysis. Each analysis by this procedure requires 70 minutes for the gradient separation and 20 minutes to re-equilibrate the column for a total HPLC turnaround time of 90 minutes. The rationale and approach to peak integration for determination of deamidated DNase in a sample are described below.

Deamidation of human DNase occurs at least at the asparagine residue that is present at amino acid position 74 (Asn-74) in native mature human DNase. Asn-74 is on the C-terminal side of a tryptic cleavage site at the arginine residue at amino acid position 73 (Arg-73), as seen in the list of expected tryptic peptides of human DNase shown in Table I.

TABLE I

PEPTIDES EXPECTED TO BE PRODUCED UPON DIGESTION OF NATIVE MATURE HUMAN DNASE WITH TRYPSIN.

| ID | Residues | Amino Acid Sequence of Peptide |
|---|---|---|
| T1 | 1-2 | LK |
| T2 | 3-15 | IAAFNIQTFGETK (SEQ.ID.NO. 3) |
| T3 | 16-31 | MSNATLVSYIVQILSR (SEQ.ID.NO. 4) |
| T4 | 32-41 | YDIALVQEVR (SEQ.ID.NO. 5) |
| T5 | 42-50 | DSHLTAVGK (SEQ.ID.NO. 6) |
| T6 | 51-73 | LLDNLNQDAPDTYHYVVSEPLGR (SEQ.ID.NO. 7) |
| T7 | 74-77 | NSYK (SEQ.ID.NO. 8) |
| T8 | 78-79 | ER |
| T9 | 80-111 | YLFVYRPDQVSAVDSYYYDDGCEPCGNDTFNR (SEQ.ID.NO. 9) |
| T10 | 112-117 | EPAIVR (SEQ.ID.NO. 10) |
| T11 | 118-121 | FFSR (SEQ.ID.NO. 11) |
| T12 | 122-126 | FTEVR (SEQ.ID.NO. 12) |
| T13 | 127-157 | EFAIVPLHAAPGDAVAEIDALYDVYLDVQEK (SEQ.ID.NO. 13) |
| T14 | 158-185 | WGLEDVMLMGDFNAGCSYVRPSQWSSIR (SEQ.ID.NO. 14) |
| T15 | 186-213 | LWTSPTFQWLIPDSADTTATPTHCAYDR (SEQ.ID.NO. 15) |
| T16 | 214-222 | IVVAGMLLR (SEQ.ID.NO. 16) |
| T17 | 223-260 | GAVVPDSALPFNFQAAYGLSDQLAQAISDHYPVEVMLK (SEQ.ID.NO. 17) |

Figure 4:
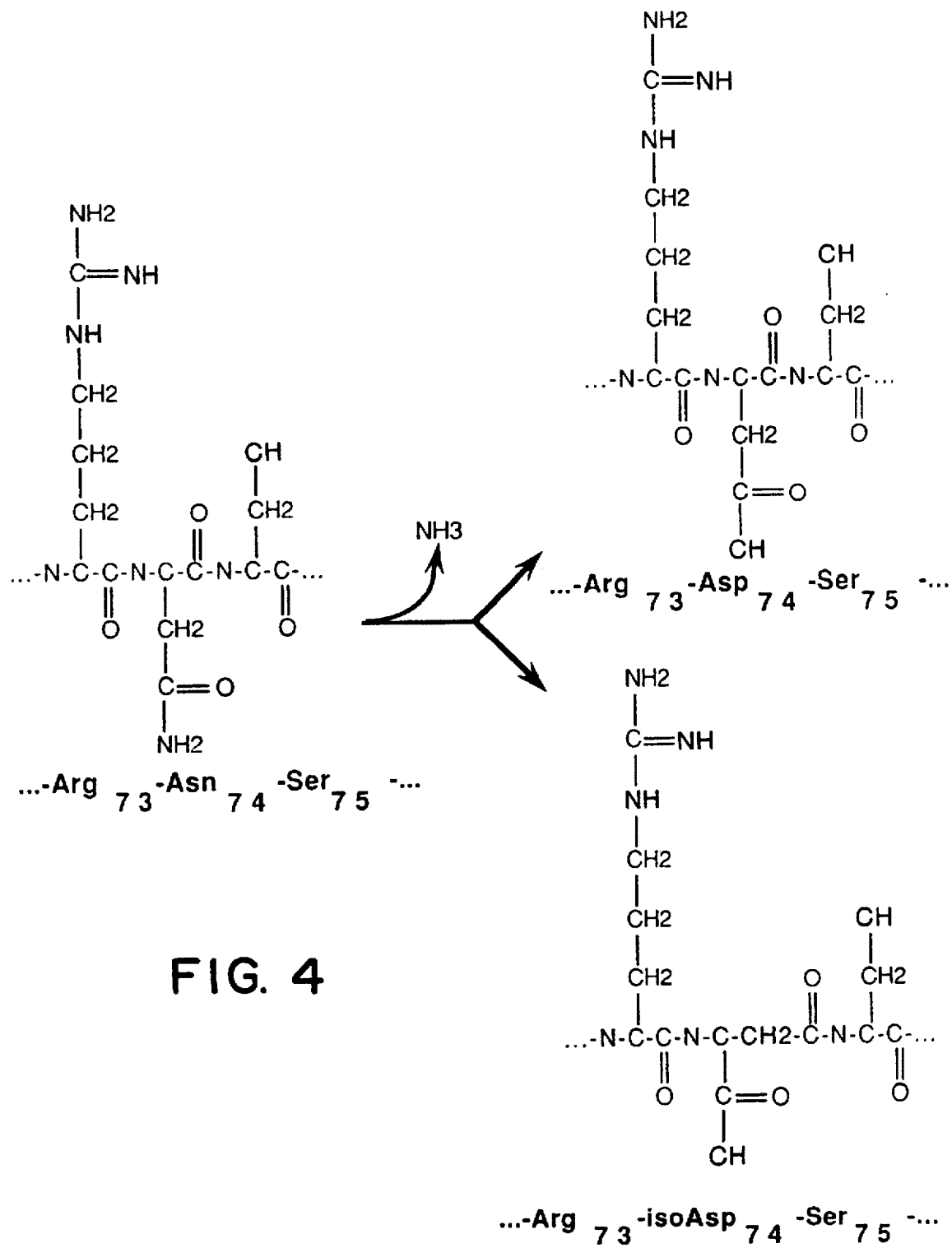
FIG. 4 is a schematic representation of the deamidation of the asparagine residue at amino acid position 74 (Asn-74) in native human DNase. Deamidation converts the Asn-74 to either an aspartic acid (Asp) or an iso-aspartate (iso-Asp) residue. Each of the three forms of DNase yields, on digestion with trypsin, a pair of peptides that indicates the identity of the particular form of DNase.

Instead of the Asn (single letter designation "N") residue at residue 74 in native, non-deamidated human DNase, deamidated human DNase has either an Aso or iso-Asp residue, as shown in FIG. 4. Iso-Asp is an isomeric, beta-amino acid form of aspartic acid. The peptide bond between Arg-73 and iso-Asp is resistant to cleavage by trypsin, so deamidated human DNase yields a characteristic tryptic peptide containing residues 51-77 and called T6-7 since it is the conjoined peptides T6 and T7. Under conditions employed for tryptic mapping, the Arg-73-Asn-74 peptide bond in non-deamidated human DNase and the Arg-73-Asp-74 peptide bond in the Asp form of deamidated human DNase are cleaved by trypsin. Hence, non-deamidated DNase is indicated in the tryptic map by the presence of T7 peptide shown in Table I, while the Asp-74 form of deamidated human DNase is indicated in the tryptic map by the presence of the deamidated T7 peptide, called (D)T7. These three reporter peptides are labelled in FIG. 3. Unfortunately, trypsin only partially cleaves the peptide bond at the C-terminal side of T7, between residues 77 and 78, so that each of the reporter peptides T7, (D)T7 and T6-7 has a T8-conjugate, T7-8, (D)T7-8 and T6-7-8, respectively. These six reporter peptides must therefore be accounted for in order to quantitate deamidated human DNase by the tryptic mapping method.

In principle, the (D)T7, (D)T7-8, T6-7 and T6-7-8 peptides represent deamidated human DNase and the T7 and T7-8 peptides represent non-deamidated human DNase and knowledge of the relative proportions of these peptides permits a straightforward calculation of the extent of deamidation in a preparation of DNase. In order to calculate the fraction of the sample that is deamidated DNase, knowledge of the molar ratios of deamidated and non-deamidated species is required, but the tryptic map gives peak areas of individual peptides, not molar amounts. There are two additional problems in the tryptic mapping procedure that must be overcome: one chromatographic problem and one detection problem. The chromatographic problem is that the T2 peptide coelutes with T6-7, and so impedes the integration of an accurate peak area of this deamidation-indicating peptide. This problem can be overcome by integration of the chromatogram obtained at 280 nm, since all six of the relevant peptides have at least one tyrosine (Tyr) residue, and so absorb strongly at 280 nm, while T2 contains no Tyr or tryptophan (Trp) residues and thus absorbs negligibly at this wavelength. The detection problem is that the T6-7 and T6-7-8 peptides each contain three Tyr residues while the other four peptides each contain only one. Thus the T6-containing peptides have a higher molar absorptivity than do the peptides that contain only T7, and a simple comparison of peak areas would tend to overestimate the content of deamidated species in a sample. This problem is overcome by normalizing the peak areas of the six peptides to the number of Tyr residues in the peptide. Normalizing the peak areas in this manner implies that all tyrosine residues in each of the peptides is in an equivalent chemical environment, which is probably a good assumption for relatively small peptides such as considered here. Upon normalization, the corrected peak areas for deamidated and non-deamidated peptides can be compared to arrive at an estimate of the content of deamidated DNase in a sample.

2. Tentacle Cation Exchange Chromatography.

Tentacle cation exchange (TCX) resins, unlike conventional cation exchange resins, have polyionic ligands bound to a silica surface. The ligands of the LiChrospher® 1000 $SO_3^-$ column (EM Separations, Gibbstown, N.J.) used in this example are advertised as containing between 25 and 50 sulfopropyl groups along a polyethylene backbone that is joined at one end to the silica surface.

Figure 5:
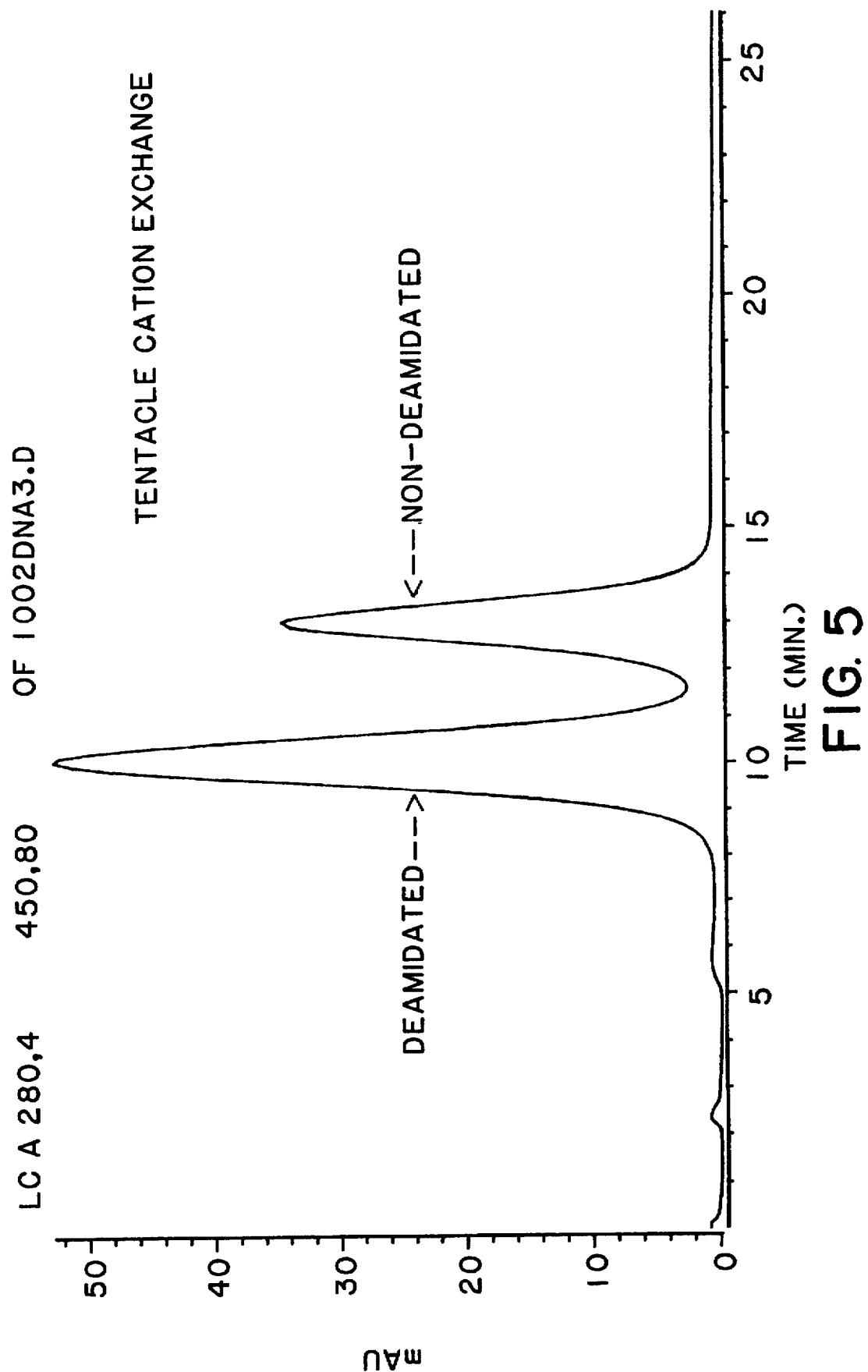
FIG. 5 is a chromatogram of a human DNase sample fractionated on a tentacle cation exchange (TCX) column. The sample shown is 67% deamidated DNase.

The TCX chromatogram of a sample of recombinant human DNase run on a LiChrospher® 1000 $SO_3^-$ column is shown in FIG. 5. Recombinant human DNase was purified from cultures of Chinese hamster ovary (CHO) cells transformed with DNA encoding human DNase. Shak, et al., Proc. Nat. Acad. Sci. 87:9188-9192 (1990); Shak, et al., International Patent Application Publication No. WO 90/07572 (published 12 Jul. 1990).

Figure 6:
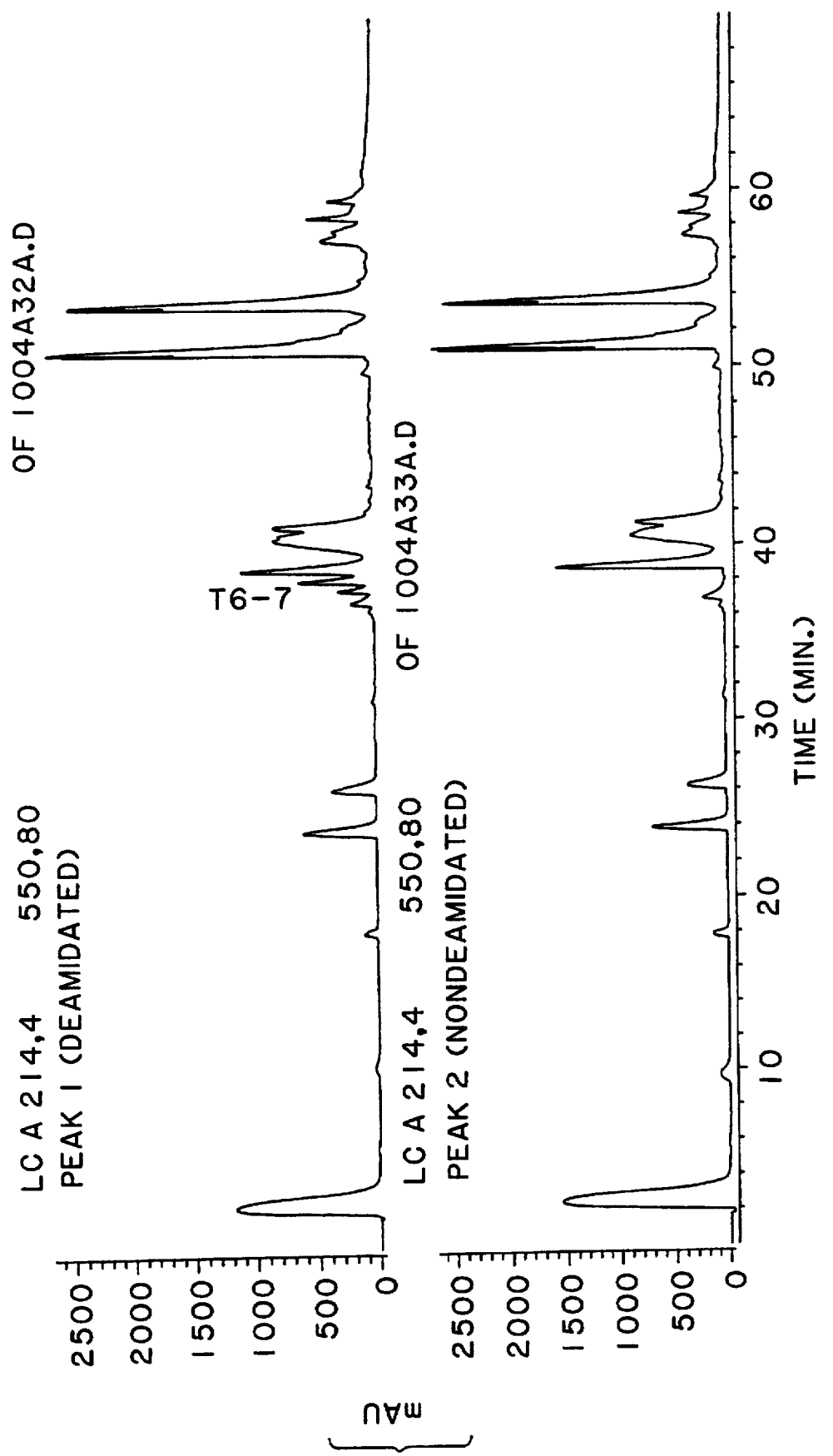
FIG. 6 shows tryptic maps of the two peak fractions from the TCX separation shown in FIG. 5. The absence of tryptic peptide T6-7 from the map of the Peak 2 digest indicates the absence of deamidated DNase.

The two peaks obtained were collected and subjected to several analyses in order to identify them as the forms of DNase differing only at the residue at amino acid position 74. FIG. 6 shows tryptic maps of the two peaks collected from the TCX column, confirming that they are, respectively, the deamidated and non-deamidated forms of human DNase. The tryptic map also reveals that both forms of deamidated DNase (having Asp and iso-Asp at amino acid position 74) are present in the first peak from the TCX separation. Table II shows the specific activities measured for the two peaks, confirming the relationship between deamidation and specific activity inferred from the correlation shown in FIG. 2, and further supporting the identification of the TCX fractions. Activity of the DNase fraction was determined by a methyl green (MG) assay.

TABLE II

ACTIVITIES OF FRACTIONS COLLECTED FROM
TCX COLUMN
MG and ELISA concentrations are the averages of
determinations on two samples.

| Sample | MG (μg/ml) | ELISA (μg/ml) | Specific Activity |
|---|---|---|---|
| Starting preparation of recombinant human Dnase (load) | 8315 | 7828 | 1.06 |
| TCX Peak 1 (deamidated) | 85.3 | 119.7 | 0.71 |
| TCX Peak 2 (non-deamidated) | 149.2 | 99.4 | 1.50 |

Figure 7:
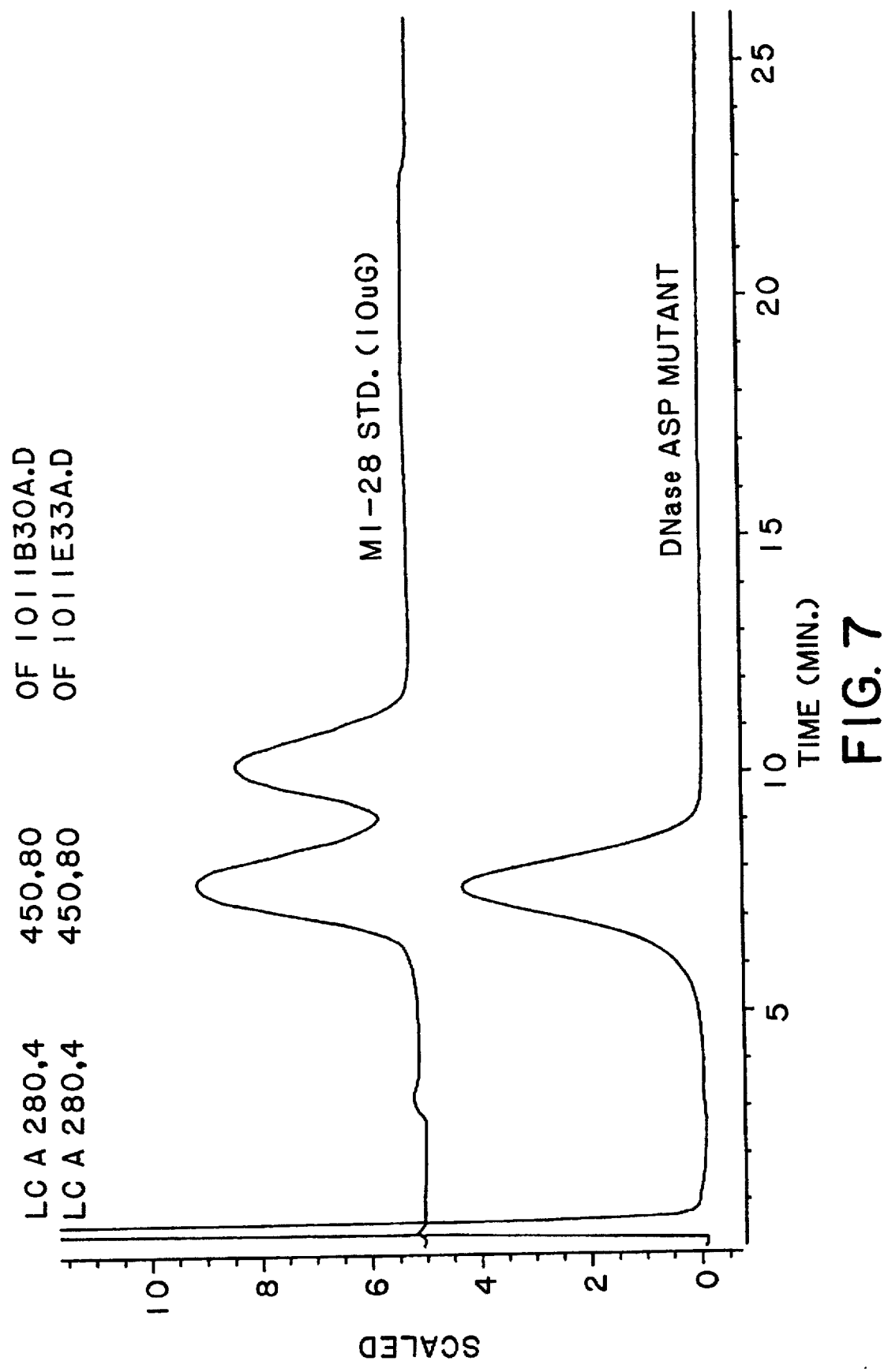
FIG. 7 shows chromatograms of several human DNase samples fractionated on a TCX column. The sample designated "M1-28 STD." is a preparation of human DNase obtained from a culture of Chinese hamster ovary (CHO) cells transformed with DNA encoding native human DNase I. The sample designated "DNase ASP Mutant" is DNase having an aspartic acid residue (rather than an asparagine residue) at amino acid position 74, and which thus has the same amino acid sequence as the Asp form of deamidated DNase shown in FIG. 4. The DNase ASP Mutant was obtained from a culture of cells transformed with DNA encoding that mutant form of human DNase. The DNA encoding the DNase ASP Mutant was prepared by site-directed mutagenesis of DNA encoding native human DNase. Comparison of the chromatograms shows that one of the forms of human DNase in the M1-28 STD. elutes from the TCX column at the same position as the DNase Asp Mutant.

A mutant form of human DNase, having an Asp residue at amino acid position 74, was produced by site-directed mutagenesis of the DNA encoding native mature human DNase. This mutant coelutes with the first peak obtained in the above chromatography, as shown in FIG. 7.

The following is the procedure used to pack the LiChrospher® 1000 $SO_3^-$ tentacle cation exchange resin. Another tentacle cation exchange resin similarly useful for separation of deamidated and non-deamidated forms of human DNase is Fractogel® tentacle cation exchange resin (EM Separations, Gibbstown, N.J.). LiChrospher and Fractogel are registered trademarks of EM Industries, Inc., Hawthorne, N.Y., or E. Merck, Darmstadt, West Germany. The "strong" forms of the tentacle cation exchange resins (whether LiChrospher or Fractogel), having a $SO_3^-$ functional group, appear at this time to give the best results.

3. HPLC Column Packing Procedure for LiChrospher® 1000 $SO_3^-$ Resin.

a. Materials and Equipment:
 1. Superformance glass cartridge 1.0 cm×5.0 cm bed.
 2. Packing Buffer: 10 mM sodium acetate, 1 mM $CaCl_2$, pH to 4.5 with acetic acid. Filter through a 0.2μ filter.
 3. Column packing reservoir with a capacity of 20 ml. (Alltech part #9501 or equivalent).
 4. Empty 4.6 mm×50 mm stainless steel column with 0.5 μ cut-off frits
 5. HPLC pump capable of maintaining a back pressure of 2000 psi (Waters Model 510 or equivalent).

b. Packing Procedure.
 1. De-fine resin:
  a) Unpack 1.0 cm×5.0 cm Superformance glass column (Bed volume=3.93 ml resin). Resuspend resin to 20 mls in a clear glass, capped vessel with column packing buffer. Slurry into a uniform suspension and divide into 2×10 ml aliquots. Add 10 mls of column packing buffer to each aliquot to achieve suspensions of approx. 1.95 mls resin in 20 mls packing buffer.
  b) Slurry resin to achieve a uniform suspension. Allow to settle until particles form a solid bed on the bottom of the vessel (2–4 hours). Carefully pour off the supernatant containing fine particles.
  c) Add 20 mls. packing buffer to resin and repeat step b). This procedure should be repeated at least four times to assure removal of all fine resin particles.
 2. Column Packing:
  a) Connect 4.6 mm×50 mm empty HPLC column to packing reservoir. Slurry resin in 20 mls of packing buffer.
  b) Add slurried resin to reservoir and quickly cap. Pump packing buffer at a pressure that does not exceed 2000 psi. Adjust flow rate so that packing pressure remains constant at about 2000 psi and flow for 15 minutes after pressure stabilizes. Remove column and attach top end. Column may be used directly or stored in 0.02% sodium azide.

For most samples, including DNase formulated in 150 mM NaCl, no sample preparation is required prior to injection of the sample onto the column. The column is equilibrated with a pH 4.5 acetate buffer containing calcium ions, the sample is injected, and the column then is eluted with a salt gradient. The following procedure is useful for small-scale separations of deamidated and non-deamidated forms of human DNase. The proportions of the peak areas on the resulting chromatogram are equal to the proportions of deamidated and non-deamidated DNase in the sample.

Step 1. Load sample, containing up to 150 mM NaCl and at a pH up to 9 into autosampler vial. Harvested cell culture fluid samples require adjustment of pH to 4.5 and centrifugation to remove proteins that are insoluble in the buffers used in this procedure.

Step 2. Separate the two forms of DNase by HPLC under the following conditions:
 Column: TCX LiChrospher® 1000 $SO_3^-$ repacked into a steel column. Column dimensions of 4.6×50 mm and 4.6×150 mm have been packed and employed. Column temperature: ambient. Eluent A: 10 mM sodium acetate, 1 mM CaCl2, pH 4.5. Eluent B: 1M NaCl in buffer A. Gradient profile:

| Time (min) | % A | % B |
|---|---|---|
| 0 | 100 | 0 |
| 4 | 100 | 0 |
| 30 | 30 | 70 |
| 30.1 | 5 | 95 |
| 37 | 5 | 95 |

Flow rate: 0.8 ml/min (50 mm column), 0.5 ml/min (150 mm column). Sample injection volume: up to 250 μl. Post-run column re-equilibration time at 100% A: 20 min. Autosampler compartment temperature: 5°. Detection: Absorbance at 280 nm.

Step 3. Integrate chromatogram. Calculate the proportion of deamidated species based on the peak area of the earlier eluting deamidated DNase relative to the total peak area of both forms.

Tentacle cation exchange chromatography also provides a means for separating, at large scale, the deamidated and non-deamidated forms of human DNase. Large scale separations are more conveniently carried out using simplified elution operating conditions than are described above for small-scale analytical separations of the two forms of DNase. Hence, larger scale separations have been carried out on the Fractogel-supported tentacle cation exchanger according to the following pH-elution procedure:

Step 1. Pack 31.6 column (1.6 cm i.d.×15.7 cm high) with Fractogel EMD $SO_3$-650M tentacle cation exchange resin (EM Separations, Gibbstown, N.J.).

Step 2. Diafilter DNase load with equilibration buffer (30 mM sodium acetate (NaAc), 1 mM calcium chloride ($CaCl_2$), 50 mM sodium chloride (NaCl), pH 5). Concentrate by ultrafiltration to volume of 355 mls and concentration of 2.5 mg/ml.

Step 3. Wash column with 2.5 column volumes (CV) of 2% sodium hydroxide (NaOH).

Step 4. Wash column with 2.5 CV of pre-equilibration buffer (300 mM NaAc, 1M NaCl, pH 5).

Step 5. Wash column with 2.5 CV of equilibration buffer.

Step 6. Load column with 1–1.3 g of diafiltered ultrafiltered DNase (from Step 2). Begin collecting fractions of column effluent upon commencement of DNase load.

Step 7. Wash column with 5 CV of equilibration buffer.

Step 8. Wash column with 5 CV of pH 5.3 wash buffer (25 mM succinate, 1 mM CaCl$_2$, pH 5.3).

Step 9. Wash column with 10 CV of pH 5.4 wash buffer (25 mM succinate, 1 mM CaCl$_2$, pH 5.4).

Step 10. Wash column with 10 CV of pH 6 wash buffer (25 mM MES, 1 mM CaCl$_2$, pH 6.0).

Step 11. Combine fractions collected during Steps 6–8 to make a pool consisting predominantly of deamidated DNase. Combine fractions collected during Step 10 to make a non-deamidated DNase pool. Fractions collected during Step 9 contain a mixture of the two forms of DNase and may be recycled.

The protocol described above is one example of the use of a tentacle cation exchange resin for a preparative purification of the two forms of recombinant human DNase in a manner that is scaleable to large-scale recovery of purified deamidated and purified non-deamidated DNase.

4. Heparin and Immobilized DNA Analog Chromatography.

Figure 8:
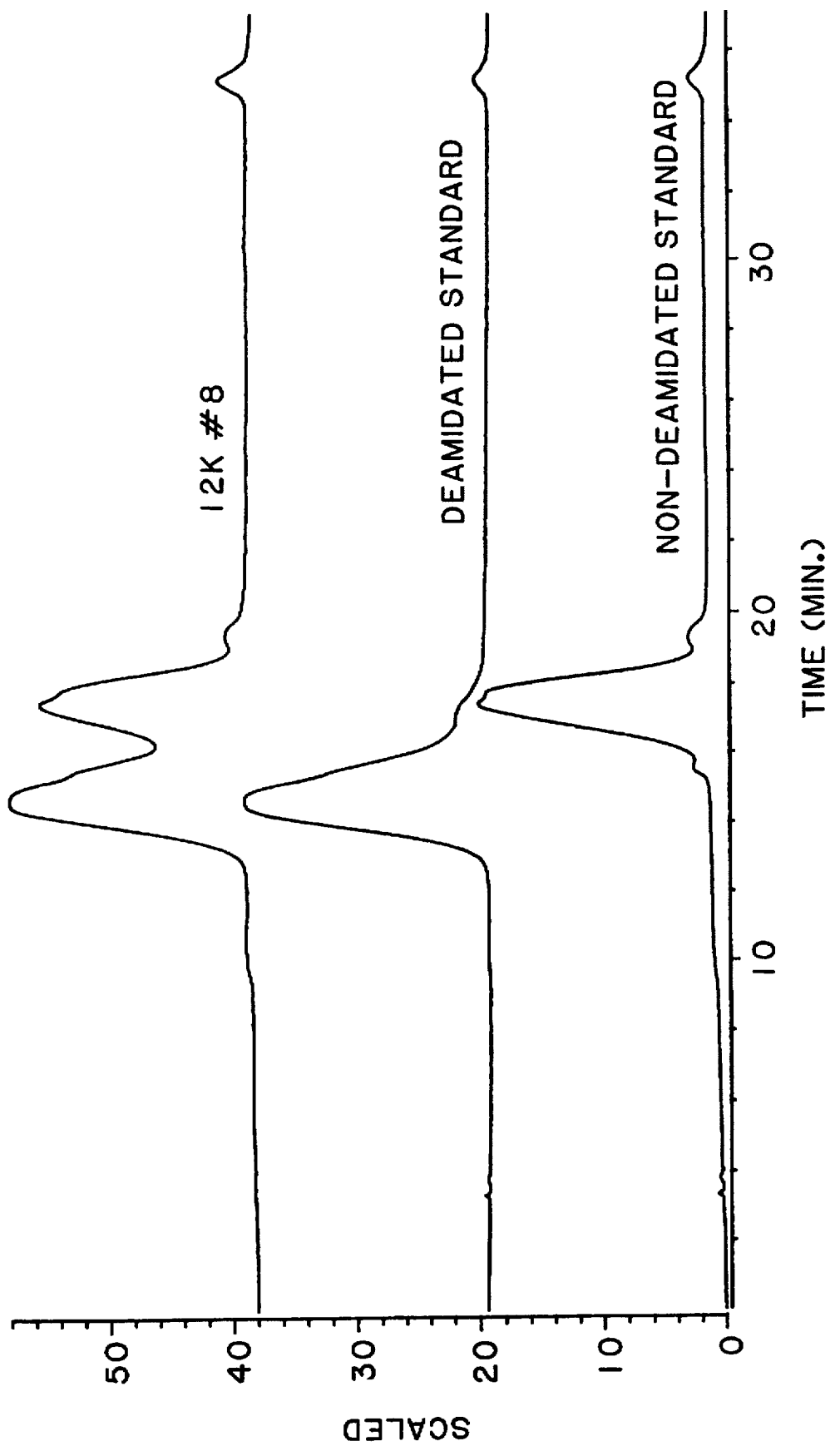
FIG. 8 shows chromatograms of several human DNase samples fractionated on a TSK-Heparin column (Toso Haas, Montgomeryville, Pa.). The sample designated "12K #8" is a preparation of human DNase obtained from a culture of Chinese hamster ovary (CHO) cells transformed with DNA encoding native human DNase I. The sample designated "Deamidated Standard" is purified deamidated human DNase. The sample designated "Non-deamidated standard" refers to purified non-deamidated human DNase. Purified deamidated human DNase and purified non-deamidated human DNase were prepared by TCX chromatography.

In FIG. 8 chromatograms are aligned of analyses on a TSK-Heparin column (Toso Haas, Montgomeryville, Pa.) of samples containing either a mixture of deamidated and non-deamidated forms of human DNase, purified deamidated human DNase, or purified non-deamidated human DNase. The TSK-Heparin column was run under the same conditions as described above for running the analytical TCX column. The aligned chromatograms demonstrate that the column of immobilized heparin resolves deamidated and non-deamidated forms of DNase.

As described above, another means of separating the deamidated and non-deamidated forms of DNase is to employ a column containing an immobilized analog of DNA that is resistant to hydrolysis by DNase. One example of this approach to an immobilized DNA analog column involved the synthesis of the phosphorothioate oligonucleotide 5'-GCGCGCGCGCGCGCGCGCGCGC-NH$_3$-3' SEQ ID NO:18. This self-complementary sequence can be annealed into a double-stranded form, and coupled to a Rainin Hydropore-EP column (Rainin Co., Woburn, Mass.). FIG. 9 shows aligned chromatograms of the analyses on this column of samples containing either a mixture of deamidated and non-deamidated forms of human DNase, purified deamidated human DNase, purified non-deamidated human DNase, or purified mutant human DNase having an aspartic acid residue (rather than an asparagine residue) at amino acid position 74. The column was run for these analyses in a buffer containing 1 mM calcium chloride, 5 mM MES at a pH of 6, and eluted with a linear gradient in salt concentration to 1M sodium chloride over 20 minutes at a flow rate of 1 ml/min. As shown in FIG. 9, under these conditions deamidated and non-deamidated DNase forms are partially separated from each other. In addition, the two isomeric forms of deamidated DNase, that differ at amino acid position 74 of the DNase sequence by having either aspartic acid or iso-aspartic acid at this position, are also resolved by this column. Thus an additional benefit of this chromatographic method is that it allows the isolation of the two isomers that arise on deamidation of human DNase.

5. Enzymatic Activity of Deamidated Human DNase and Non-deamidated Human DNase.

Several analytical methods have been used to examine the effect of deamidation on the enzymatic activity of human DNase. Purified deamidated human DNase and purified non-deamidated human DNase for use in these studies were prepared by TCX chromatography, as described above.

In one method for determination of DNase enzymatic activity, synthetic double stranded DNA, 25 base pairs in length, was labeled with dinitrophenol (DNP) on one end and with biotin on the other end. Hydrolysis of the substrate by DNase was detected by capture of the reaction products on microtiter plate wells coated with antibody to DNP and by quantitation of the intact probe with streptavidin-horseradish peroxidase. The specific activity of stability samples was correlated ($r^2$=0.613; n=5) with the extent of DNase deamidation (range 27%–93%). Extrapolation of the least squares linear equation provided an estimate that the specific activity of deamidated human DNase was approximately 77% lower than that of non-deamidated human DNase.

Another method for determination of DNase enzymatic activity involved hydrolysis of the chromogenic substrate p-nitrophenyl phenylphosphonate (PNPP) as described by Liao, et al., Biochem. J. 255: 781–787 (1988). The kinetics of PNPP hydrolysis by human DNase are sigmoidal and were fit to the Hill equation by nonlinear regression. By this method the $V_{max}$ of fully deamidated human DNase was determined to be 77% lower than that of non-deamidated human DNase. The substrate concentration for half maximal activity ($S_{0.5}$) did not differ significantly for the deamidated and non-deamidated human DNase samples.

Another method for determination of DNase enzymatic activity is the assay described by Kunitz, J. Gen. Physiol. 33:349 (1950), preferably modified such that the enzymatic reaction is carried out at about pH 7.0–7.5. By this method, the enzymatic activity of deamidated human DNase also was determined to be lower than that of non-deamidated human DNase.

6. In Vitro Storage of Human DNase.

Human DNase purified from recombinant CHO cells was dissolved at a concentration of 4 mg/ml in an unbuffered aqueous solution of 150 mM NaCl and 1 mM CaCl$_2$. Samples of the resulting DNase solution were then placed into glass and plastic vials. Two different types of plastic vials were used, one being made of Dupont 20 plastic resin (manufactured by E.I. du Pont de Nemours & Co., Inc., Wilmington, Del. USA), and the other being made of Escorene plastic resin (manufactured by Exxon Corp.). Both of those plastics are low density polyethylene, but containers formulated with other plastics, such as polypropylene, polystyrene, or other polyolefins also may be used. The vials containing the DNase solution were stored at either −70° C., 2°–80° C., or 25° C. Initially, about 60%–65% of the DNase in the solutions was deamidated.

The DNase solutions in the vials were assayed at several times after initial storage to determine the extent of deamidation of the DNase. The results of those assays are shown in Table III.

TABLE III

% DEAMIDATION OF RECOMBINANT HUMAN DNASE STORED IN GLASS AND PLASTIC VIALS.

| Sample | Day | −70° C. | 2–8° C. | 25° C. |
|---|---|---|---|---|
| Glass | 83 | 66 | 66 | 78 |
|  | 174 | 63 | 66 | 81 |
| Dupont 20 | 83 | 65 | 66 | 71 |
|  | 174 | 63 | 63 | 70 |
| Escorene | 83 | 65 | 66 | 71 |
|  | 174 | 64 | 62 | 70 |

After 83 and 174 days storage at −70° C. or 2–8° C., no difference was found in the amount of deamidated DNase in the plastic vials and the amount of deamidated DNase in the glass vials. In each such case, approximately 64% (+/−2) of the DNase in the vials was deamidated DNase.

Unexpectedly, however, after 83 or 174 days storage at 25° C., there was a difference in the amount of deamidated DNase in the plastic vials and the amount of deamidated DNase in the glass vials. Significantly less deamidated DNase was present in the plastic vials. In particular, after 83 days storage at 25° C., 78% of the DNase in the glass vials was deamidated DNase, whereas only about 70% of the DNase in the plastic vials was deamidated DNase. After 174 days storage at 25° C., 81% of the DNase in the glass vials was deamidated DNase, whereas only about 71% of the DNase in the plastic vials was deamidated DNase.

Without limiting the invention to any particular mechanism or theory of operation, it may be that the differences in deamidation of DNase in plastic and glass vials may be a consequence of differences in the pH of the solutions in the vials. Initially, the pH of the DNase solution in the glass vials was slightly higher than that in the plastic vials (approximately pH 6.7 and approximately pH 6.5, respectively). The pH of the DNase solution in the glass vials continued to increase slightly over time (to approximately pH 6.9 after 83 days storage at 25° C., and approximately pH 7.0 after 174 days storage at 25° C.), perhaps as consequence of silicates or ions from the glass surface dissolving in the solution. At higher pH, the rate of deamidation of human DNase is increased. Since it was not appreciated that deamidation of human DNase occurs at elevated pH, it is an embodiment of this invention to formulate and/or store human DNase in solutions having acidic pH, typically at about pH 4.5–6.8 and most preferably at about pH 5.0–6.8.

Thus, a significant improvement in the stability of human DNase in solution is obtained by placing such DNase solution in plastic vials rather than glass vials, with apparently less deamidation of the DNase occurring over time in the plastic vials than in the glass vials. This finding may be especially relevant to the choice of packaging of human DNase for therapeutic use, where it is especially desirable that the human DNase be capable of storage for extended periods of time without significant loss of enzymatic activity. Of course, glass vials with non-glass coatings, for example, plastic linings, would be equally useful. What is important is to avoid storing DNase in contact with glass, especially for storage exceeding about 15–30 days.

General Remarks

The foregoing description details specific methods which can be employed to practice the present invention. Having detailed specific methods used to identify, characterize, separate and use the pure deamidated and non-deamidated human DNase hereof, and further disclosure as to specific model systems pertaining thereto, those skilled in the art will well enough know how to devise alternative reliable methods for arriving at the same information in using the fruits of the present invention. Thus, however detailed the forgoing may appear in text, it should not be construed as limiting the overall scope hereof; rather, the ambit of the present invention is to be determined only by the lawful construction of the appended claims.

---

What is claimed is:

1. A process comprising separating deamidated and non-deamidated human DNase by use of a tentacle cation exchange resin.

2. A process comprising separating deamidated and non-deamidated human DNase by use of an immobilized heparin resin.

3. A process comprising separating deamidated and non-deamidated human DNase by use of an immobilized non-hydrolyzable DNA analog resin.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 346 amino acids
        ( B ) TYPE: Amino Acid
        ( D ) TOPOLOGY: Linear ( x i ) SEQUENCE DESCRIPTION: SEQ ID NO:1:

```
Ser  Cys  Thr  Gly  Ser  Ala  Leu  Lys  Cys  Phe  Phe  Arg  Asp  Leu  Ser
  1                  5                      10                         15

Ser  Xaa  Thr  Thr  Phe  Phe  Ser  Leu  Ser  Ser  Lys  Arg  Arg  Lys  Leu
                     20                      25                         30

Ser  Ser  Lys  Asp  Ile  Pro  Asp  Ser  Xaa  Gln  His  Ser  Arg  His  Leu
                     35                      40                         45

Xaa  Gly  His  His  His  His  Leu  Arg  Met  Arg  Gly  Met  Lys  Leu  Leu
                     50                      55                         60

Gly  Ala  Leu  Leu  Ala  Leu  Ala  Ala  Leu  Leu  Gln  Gly  Ala  Val  Ser
                     65                      70                         75
```

| | | | | | | | | | | | | | | |
|---|---|---|---|---|---|---|---|---|---|---|---|---|---|---|
| Leu | Lys | Ile | Ala | Ala<br>80 | Phe | Asn | Ile | Gln | Thr<br>85 | Phe | Gly | Glu | Thr | Lys<br>90 |
| Met | Ser | Asn | Ala | Thr<br>95 | Leu | Val | Ser | Tyr | Ile<br>100 | Val | Gln | Ile | Leu | Ser<br>105 |
| Arg | Tyr | Asp | Ile | Ala<br>110 | Leu | Val | Gln | Glu | Val<br>115 | Arg | Asp | Ser | His | Leu<br>120 |
| Thr | Ala | Val | Gly | Lys<br>125 | Leu | Leu | Asp | Asn | Leu<br>130 | Asn | Gln | Asp | Ala | Pro<br>135 |
| Asp | Thr | Tyr | His | Tyr<br>140 | Val | Val | Ser | Glu | Pro<br>145 | Leu | Gly | Arg | Asn | Ser<br>150 |
| Tyr | Lys | Glu | Arg | Tyr<br>155 | Leu | Phe | Val | Tyr | Arg<br>160 | Pro | Asp | Gln | Val | Ser<br>165 |
| Ala | Val | Asp | Ser | Tyr<br>170 | Tyr | Tyr | Asp | Asp | Gly<br>175 | Cys | Glu | Pro | Cys | Gly<br>180 |
| Asn | Asp | Thr | Phe | Asn<br>185 | Arg | Glu | Pro | Ala | Ile<br>190 | Val | Arg | Phe | Phe | Ser<br>195 |
| Arg | Phe | Thr | Glu | Val<br>200 | Arg | Glu | Phe | Ala | Ile<br>205 | Val | Pro | Leu | His | Ala<br>210 |
| Ala | Pro | Gly | Asp | Arg<br>215 | Val | Ala | Glu | Ile | Asp<br>220 | Ala | Leu | Tyr | Asp | Val<br>225 |
| Tyr | Leu | Asp | Val | Gln<br>230 | Glu | Lys | Trp | Gly | Leu<br>235 | Glu | Asp | Val | Met | Leu<br>240 |
| Met | Gly | Asp | Phe | Asn<br>245 | Ala | Gly | Cys | Ser | Tyr<br>250 | Val | Arg | Pro | Ser | Gln<br>255 |
| Trp | Ser | Ser | Ile | Arg<br>260 | Leu | Trp | Thr | Ser | Pro<br>265 | Thr | Phe | Gln | Trp | Leu<br>270 |
| Ile | Pro | Asp | Ser | Ala<br>275 | Asp | Thr | Thr | Ala | Thr<br>280 | Pro | Thr | His | Cys | Ala<br>285 |
| Tyr | Asp | Arg | Ile | Val<br>290 | Val | Ala | Gly | Met | Leu<br>295 | Leu | Arg | Gly | Ala | Val<br>300 |
| Val | Pro | Asp | Ser | Ala<br>305 | Leu | Pro | Phe | Asn | Phe<br>310 | Gln | Ala | Ala | Tyr | Gly<br>315 |
| Leu | Ser | Asp | Gln | Leu<br>320 | Ala | Gln | Ala | Ile | Ser<br>325 | Asp | His | Tyr | Pro | Val<br>330 |
| Glu | Val | Met | Leu | Lys<br>335 | Xaa | Ala | Ala | Pro | Pro<br>340 | His | Thr | Ser | Xaa | Thr<br>345 |
| Ala<br>346 | | | | | | | | | | | | | | |

( 2 ) INFORMATION FOR SEQ ID NO:2:

( i ) SEQUENCE CHARACTERISTICS:
  ( A ) LENGTH: 1039 base pairs
  ( B ) TYPE: Nucleic Acid
  ( C ) STRANDEDNESS: Single
  ( D ) TOPOLOGY: Linear ( x i ) SEQUENCE DESCRIPTION: SEQ ID NO:2:

```
TCCTGCACAG GCAGTGCCTT GAAGTGCTTC TTCAGAGACC TTTCTTCATA          50

GACTACTTTT TTTTCTTTAA GCAGCAAAAG GAGAAAATTG TCATCAAAGG         100

ATATTCCAGA TTCTTGACAG CATTCTCGTC ATCTCTGAGG ACATCACCAT         150

CATCTCAGGA TGAGGGGCAT GAAGCTGCTG GGGCGCTGC  TGGCACTGGC         200

GGCCCTACTG CAGGGGGCCG TGTCCCTGAA GATCGCAGCC TTCAACATCC         250

AGACATTTGG GGAGACCAAG ATGTCCAATG CCACCCTCGT CAGCTACATT         300
```

```
GTGCAGATCC  TGAGCCGCTA  TGACATCGCC  CTGGTCCAGG  AGGTCAGAGA      350

CAGCCACCTG  ACTGCCGTGG  GGAAGCTGCT  GGACAACCTC  AATCAGGATG      400

CACCAGACAC  CTATCACTAC  GTGGTCAGTG  AGCCACTGGG  ACGGAACAGC      450

TATAAGGAGC  GCTACCTGTT  CGTGTACAGG  CCTGACCAGG  TGTCTGCGGT      500

GGACAGCTAC  TACTACGATG  ATGGCTGCGA  GCCTGCGGG   AACGACACCT      550

TCAACCGAGA  GCCAGCCATT  GTCAGGTTCT  TCTCCCGGTT  CACAGAGGTC      600

AGGGAGTTTG  CCATTGTTCC  CCTGCATGCG  GCCCGGGGG   ACCGAGTAGC      650

CGAGATCGAC  GCTCTCTATG  ACGTCTACCT  GGATGTCCAA  GAGAAATGGG      700

GCTTGGAGGA  CGTCATGTTG  ATGGGCGACT  TCAATGCGGG  CTGCAGCTAT      750

GTGAGACCCT  CCCAGTGGTC  ATCCATCCGC  CTGTGGACAA  GCCCCACCTT      800

CCAGTGGCTG  ATCCCCGACA  GCGCTGACAC  CACAGCTACA  CCCACGCACT      850

GTGCCTATGA  CAGGATCGTG  GTTGCAGGGA  TGCTGCTCCG  AGGCGCCGTT      900

GTTCCCGACT  CGGCTCTTCC  CTTTAACTTC  CAGGCTGCCT  ATGGCCTGAG      950

TGACCAACTG  GCCCAAGCCA  TCAGTGACCA  CTATCCAGTG  GAGGTGATGC     1000

TGAAGTGAGC  AGCCCCTCCC  CACACCAGTT  GAACTGCAG                  1039
```

(2) INFORMATION FOR SEQ ID NO:3:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO:3:

```
Ile  Ala  Ala  Phe  Asn  Ile  Gln  Thr  Phe  Gly  Glu  Thr  Lys
 1              5                        10             13
```

(2) INFORMATION FOR SEQ ID NO:4:

(i) SEQUENCE CHARACTERISTICS:
        (A) LENGTH: 16 amino acids
        (B) TYPE: Amino Acid
        (D) TOPOLOGY: Linear (xi) SEQUENCE DESCRIPTION: SEQ ID NO:4:

```
Met  Ser  Asn  Ala  Thr  Leu  Val  Ser  Tyr  Ile  Val  Gln  Ile  Leu  Ser
 1              5                        10                       15
Arg
16
```

(2) INFORMATION FOR SEQ ID NO:5:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO:5:

```
Tyr  Asp  Ile  Ala  Leu  Val  Gln  Glu  Val  Arg
 1              5                        10
```

(2) INFORMATION FOR SEQ ID NO:6:

(i) SEQUENCE CHARACTERISTICS:
        (A) LENGTH: 9 amino acids
        (B) TYPE: Amino Acid
        (D) TOPOLOGY: Linear ( x i ) SEQUENCE DESCRIPTION: SEQ ID NO:6:

Asp Ser His Leu Thr Ala Val Gly Lys
 1           5                     9

( 2 ) INFORMATION FOR SEQ ID NO:7:

( i ) SEQUENCE CHARACTERISTICS:
        ( A ) LENGTH: 23 amino acids
        ( B ) TYPE: Amino Acid
        ( D ) TOPOLOGY: Linear ( x i ) SEQUENCE DESCRIPTION: SEQ ID NO:7:

Leu Leu Asp Asn Leu Asn Gln Asp Ala Pro Asp Thr Tyr His Tyr
 1           5                   10                      15

Val Val Ser Glu Pro Leu Gly Arg
             20          23

( 2 ) INFORMATION FOR SEQ ID NO:8:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:8:

Asn Ser Tyr Lys
 1           4

( 2 ) INFORMATION FOR SEQ ID NO:9:

( i ) SEQUENCE CHARACTERISTICS:
        ( A ) LENGTH: 32 amino acids
        ( B ) TYPE: Amino Acid
        ( D ) TOPOLOGY: Linear ( x i ) SEQUENCE DESCRIPTION: SEQ ID NO:9:

Tyr Leu Phe Val Tyr Arg Pro Asp Gln Val Ser Ala Val Asp Ser
 1           5                   10                      15

Tyr Tyr Tyr Asp Asp Gly Cys Glu Pro Cys Gly Asn Asp Thr Phe
             20                  25                      30

Asn Arg
 32

( 2 ) INFORMATION FOR SEQ ID NO:10:

( i ) SEQUENCE CHARACTERISTICS:
        ( A ) LENGTH: 6 amino acids
        ( B ) TYPE: Amino Acid
        ( D ) TOPOLOGY: Linear ( x i ) SEQUENCE DESCRIPTION: SEQ ID NO:10:

Glu Pro Ala Ile Val Arg
 1               5   6

( 2 ) INFORMATION FOR SEQ ID NO:11:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:11:

Phe Phe Ser Arg
 1           4

(2) INFORMATION FOR SEQ ID NO:12:

(i) SEQUENCE CHARACTERISTICS:
        (A) LENGTH: 5 amino acids
        (B) TYPE: Amino Acid
        (D) TOPOLOGY: Linear (xi) SEQUENCE DESCRIPTION: SEQ ID NO:12:

```
Phe  Thr  Glu  Val  Arg
 1                    5
```

(2) INFORMATION FOR SEQ ID NO:13:

(i) SEQUENCE CHARACTERISTICS:
        (A) LENGTH: 31 amino acids
        (B) TYPE: Amino Acid
        (D) TOPOLOGY: Linear (xi) SEQUENCE DESCRIPTION: SEQ ID NO:13:

```
Glu  Phe  Ala  Ile  Val  Pro  Leu  His  Ala  Ala  Pro  Gly  Asp  Ala  Val
 1                    5                        10                        15

Ala  Glu  Ile  Asp  Ala  Leu  Tyr  Asp  Val  Tyr  Leu  Asp  Val  Gln  Glu
                     20                        25                        30

Lys
 31
```

(2) INFORMATION FOR SEQ ID NO:14:

(i) SEQUENCE CHARACTERISTICS:
        (A) LENGTH: 28 amino acids
        (B) TYPE: Amino Acid
        (D) TOPOLOGY: Linear (xi) SEQUENCE DESCRIPTION: SEQ ID NO:14:

```
Trp  Gly  Leu  Glu  Asp  Val  Met  Leu  Met  Gly  Asp  Phe  Asn  Ala  Gly
 1                    5                        10                        15

Cys  Ser  Tyr  Val  Arg  Pro  Ser  Gln  Trp  Ser  Ser  Ile  Arg
                     20                        25             28
```

(2) INFORMATION FOR SEQ ID NO:15:

(i) SEQUENCE CHARACTERISTICS:
        (A) LENGTH: 28 amino acids
        (B) TYPE: Amino Acid
        (D) TOPOLOGY: Linear (xi) SEQUENCE DESCRIPTION: SEQ ID NO:15:

```
Leu  Trp  Thr  Ser  Pro  Thr  Phe  Gln  Trp  Leu  Ile  Pro  Asp  Ser  Ala
 1                    5                        10                        15

Asp  Thr  Thr  Ala  Thr  Pro  Thr  His  Cys  Ala  Tyr  Asp  Arg
                     20                        25             28
```

(2) INFORMATION FOR SEQ ID NO:16:

(i) SEQUENCE CHARACTERISTICS:
        (A) LENGTH: 9 amino acids
        (B) TYPE: Amino Acid
        (D) TOPOLOGY: Linear (xi) SEQUENCE DESCRIPTION: SEQ ID NO:16:

```
Ile  Val  Val  Ala  Gly  Met  Leu  Leu  Arg
 1                    5                    9
```

(2) INFORMATION FOR SEQ ID NO:17:

(i) SEQUENCE CHARACTERISTICS:
    (A) LENGTH: 38 amino acids
    (B) TYPE: Amino Acid
    (D) TOPOLOGY: Linear (xi) SEQUENCE DESCRIPTION: SEQ ID NO:17:

```
Gly Ala Val Val Pro Asp Ser Ala Leu Pro Phe Asn Phe Gln Ala
 1               5                  10                  15

Ala Tyr Gly Leu Ser Asp Gln Leu Ala Gln Ala Ile Ser Asp His
                20                  25                  30

Tyr Pro Val Glu Val Met Leu Lys
                35          38
```

(2) INFORMATION FOR SEQ ID NO:18:

(i) SEQUENCE CHARACTERISTICS:
        (A) LENGTH: 22 base pairs
        (B) TYPE: Nucleic Acid
        (C) STRANDEDNESS: Single
        (D) TOPOLOGY: Linear (xi) SEQUENCE DESCRIPTION: SEQ ID NO:18:

GCGCGCGCGC GCGCGCGCGC GC      22